United States Patent [19]

Olesen et al.

[11] Plant 4,940

[45] Nov. 16, 1982

[54] ROSE PLANT

[76] Inventors: Pernille Olesen; Mogens Olesen, both of 58 Kelleriisvej, DK 3490 Kvistgaard, Denmark

[21] Appl. No.: 278,185

[22] Filed: Jun. 29, 1981

[51] Int. Cl.[3] ..... A01H 5/00

[52] U.S. Cl. ..... Plt./11

[58] Field of Search ..... Plt./11, 18, 19, 20, Plt./21

*Primary Examiner*—James R. Feyrer

*Attorney, Agent, or Firm*—Vincent G. Gioia

[57] ABSTRACT

A new hybrid tea rose variety of orange red to smoky red coloring, darkening to near currant red upon aging.

1 Drawing Figure

The present invention relates to a new and distinct variety of rose plant of the hybrid tea rose class, which was originated by my crossing as seed parent and pollen parent two unnamed, unpatented seedlings of my creation.

Among the novel characteristics possessed by this new variety which distinguish it from its parents and all other varieties of which I am aware are flowers of brilliant neyron rose coloring borne on a vigorous disease resistant plant. The flower's unique coloring combines relatively lighter toned outer petals with deeper toned coloring at flower center retaining this tonality through the exhibition stage. Flowers are exceptionally long lasting on the plant and as a cut flower. Asexual reproduction by budding of the new variety as performed in Clackamas County, Oreg., shows that the foregoing and other distinguishing characteristics come true to form and are established and transmitted through succeeding propagations.

The accompanying drawing shows typical specimens of the vegetative growth and flowers of the new variety in different stages of development and as depicted in color as nearly true as it is reasonably possible to make the same in a color illustration of this character.

The following is a detailed description of my new variety, with color terminology in accordance with the Royal Horticultural Society Color Chart (RHSCC). The terminology used in color description herein refers to plate numbers in the aforementioned color chart, e.g., "46C" is plate 46C of the Royal Horticultural Society Color Chart.

Parentage: Seedling.

*Seed parent.*—Unnamed seedling.

*Pollen parent.*—Unnamed seedling.

Class: Hybrid Tea.

The following observations are made of specimens grown outdoors in Clackamas County, Oreg. during the month of October.

FLOWER

Blooming habit: Continuous.

A. Bud:

(1) *Size.*—Large.

(2) *Form.*—Long pointed.

(3) *Color.*—Buds are near turkey red 46C to 46D as sepals divide.

(4) *Sepals.*—Long, fancy, often with numerous bractlike appendages.

(5) *Peduncle.*—Length — medium. Aspect — straight. Strength — erect, strong. Color — green.

B. Bloom:

(1) *Size.*—Average size when fully expanded — about 5 to 5½ inches.

(2) *Borne.*—Singly, rarely with side buds.

(3) *Form.*—High centered opening slowly with ruffling appearing in early stages.

(4) *Petalage.*—Number of petals under normal conditions — about 24.

(5) *Color.*—As buds open, relatively lighter colored outer petals, neyron rose 55C, are seen and in some contrast to deeper colored petals 55A at flower center which retain tonality through exhibition stage then lightening to 55C as flower ages.

C. Petals:

(1) *Texture.*—Very thick.

(2) *Appearance.*—Both sides satiny with little color variation over entire surface.

(3) *Form.*—Ovoid with slight cupping.

(4) *Arrangement.*—Regular.

(5) *Petaloids in center.*—Few, straplike.

(6) *Persistence.*—Drop off cleanly.

(7) *Fragrance.*—Slight, sweet.

(8) *Lasting quality.*—Very long lasting on plant and as cut flower.

REPRODUCTIVE ORGANS

A. Stamens, filaments and anthers:

(1) *Arrangement.*—Inner ring joined at base, regular arrangement, uneven length.

(2) *Color.*—Filaments 33B, anthers 11A.

B. Pollen:

*Color.*—12B.

C. Styles: Tightly bunched, long, color 52A.

D. Stigmas:

*Color.*—11C, small.

E. Hips:

*Shape.*—Rarely formed, when present ovoid.

*Size.*—Small.

*Color.*—146C.

*Do seeds protrude?*—Yes, almost full length.

PLANT

A. Form: Tall, upright.

B. Growth: Very vigorous, long stemmed.

*Height attained.*—About 6 feet.

C. Foliage: Compound, mostly 5 leaflets.

(1) *Size.*—Large.

(2) *Quantity.*—Abundant.

(3) *Color.*—New foliage. Upper side — near 183B. Under side — near 185C. Old foliage: Upper side — near 146A. Under side — near 139D.

(4) *Shape.*—Nearly round to oval.

(5) *Texture.*—Upper side is shiny and under side is dull, both sides veined.

(6) *Edge.*—Serrate.

(7) *Serration.*—Simple, but heavy.

(8) *Leaf stem.*—Color — near 185B. Under side — near 153B.

(9) *Stipules.*—Short, simple, pointed.

(10) *Resistance to disease.*—Blackspot — good. Mildew — excellent. Rust — excellent.

D. Wood:

(1) *New wood.*—Color — near 149B. Bark — smooth.

(2) *Old wood.*—Color — near 143C. Bark — smooth.

E. Thorns:

(1) *Thorns.*—Quantity (main stalk): ordinary. On laterals from stalk — ordinary. Form — long pointed slightly recurved. Length — varying size, short to medium. Color — near 178D. Position — irregular.

(2) *Prickles.*—Few.

F. Winter hardiness: Good winter hardiness.

I claim:

1. A new and distinct variety of rose plant of the hybrid tea class, substantially as shown and described, characterized particularly by flowers of brilliant neyron rose coloration lightening upon aging.

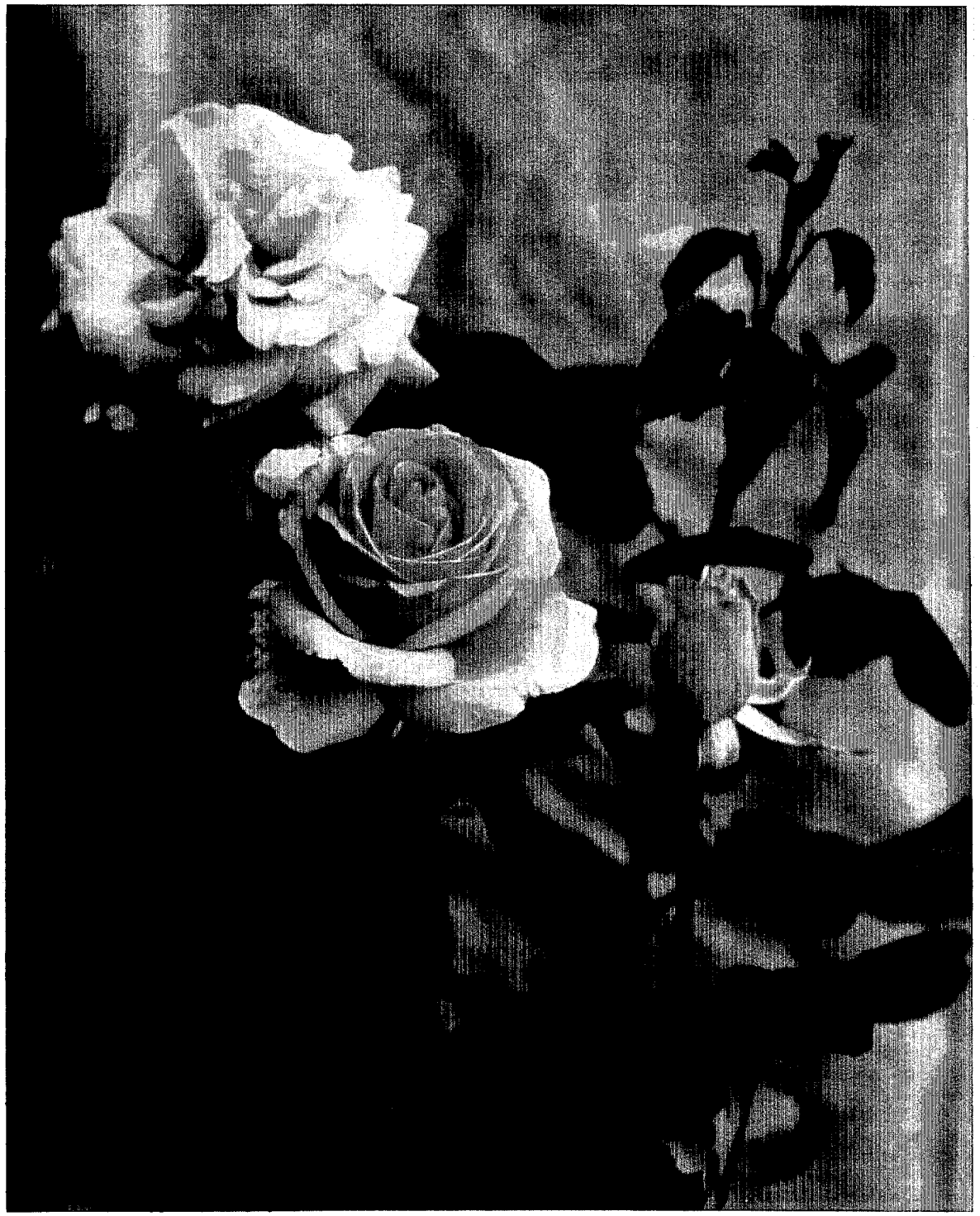

* * * * *